US006720437B2

(12) United States Patent
Jones et al.

(10) Patent No.: US 6,720,437 B2
(45) Date of Patent: Apr. 13, 2004

(54) FLUORINATED CARBOXYLIC ACID RECOVERY AND REUSE

(75) Inventors: Clay Woodward Jones, Washington, WV (US); Ta-Wei Fu, Vienna, WV (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 71 days.

(21) Appl. No.: 10/060,995

(22) Filed: Jan. 30, 2002

(65) Prior Publication Data

US 2002/0151748 A1 Oct. 17, 2002

Related U.S. Application Data

(60) Provisional application No. 60/266,952, filed on Feb. 7, 2001.

(51) Int. Cl.[7] .................................................. C11B 3/10
(52) U.S. Cl. ........................................ 554/191; 554/207
(58) Field of Search ................................ 584/207, 191

(56) References Cited

U.S. PATENT DOCUMENTS

| 3,085,083 A | 4/1963 | Schreyer |
| 3,882,153 A | 5/1975 | Seki et al. |
| 4,282,162 A | 8/1981 | Kuhls |
| 4,609,497 A | 9/1986 | Cope |
| 4,623,487 A | 11/1986 | Cope |
| 4,639,337 A | 1/1987 | Cope et al. |
| 4,908,460 A | 3/1990 | Ohsaku et al. |
| 5,043,072 A | 8/1991 | Hitotsuyanagi et al. |
| 5,312,935 A | 5/1994 | Mayer et al. |
| 5,391,709 A | 2/1995 | Egres, Jr. et al. |
| 5,442,097 A | 8/1995 | Obermeier et al. |
| 5,591,877 A | 1/1997 | Obermeier et al. |
| 5,990,330 A | * 11/1999 | Sulzbach et al. ........... 554/202 |

FOREIGN PATENT DOCUMENTS

| JP | 51119164 | 10/1976 |
| JP | 06063563 | 3/1994 |

* cited by examiner

Primary Examiner—Deborah D. Carr

(57) ABSTRACT

Fluorinated carboxylic acid, used as a surfactant in fluoropolymerization in aqueous media, can be recovered by scrubbing from the exhaust gas of the dryer during polymer drying and, after concentration and treatment with alumina, directly reused in fluoropolymerization in aqueous media.

9 Claims, No Drawings

FLUORINATED CARBOXYLIC ACID RECOVERY AND REUSE

FIELD OF THE INVENTION

This invention is in the field of recovery and recycling of fluorinated carboxylic acid used in fluoropolymerization in aqueous media.

BACKGROUND OF THE INVENTION

Polymerization of fluoroolefins to manufacture fluoropolymers is often performed in aqueous media. In one such process referred to as dispersion polymerization, fluorinated carboxylic acids are typically used as surfactants in the aqueous media at concentrations on the order of 0.1% by weight of water in the recipe. Examples of these fluorosurfactants include the perfluorinated alkanecarboxylic acids having 7 to 10 carbon atoms, in particular perfluorooctanoic acid (PFOA). These acids are generally used in the salt form, preferably as ammonium salts. Fluoropolymerization to make "granular fluoropolymer" is also done in aqueous media in a process sometimes referred to as suspension polymerization, though with less fluorosurfactant than is used in dispersion polymerization. For a discussion of the processes, see "Tetrafluoroethylene Polymers" in the Encyclopedia of Polymer Science and Engineering, John Wiley & Sons, New York, 1989, Vol. 16, p. 580.

When, after polymerization, the fluoropolymer is isolated from the aqueous medium, i.e., by coagulation in dispersion polymerization, a substantial portion of the fluorinated carboxylic acid typically remains in the fluoropolymer. When the fluoropolymer is heated for the purpose of drying, the fluorinated carboxylic acid is volatilized and carried away in the dryer or oven exhaust gas. The exhaust gas is scrubbed with water before being released to the environment. The fluorinated carboxylic acid accumulates in the scrubbing solution. In the interests of reducing emissions to the environment, and because of the considerable expense of the surfactant, it is desirable to recover the fluorinated carboxylic acid from the scrubbing solution and reuse it. Purification before reuse is necessary to avoid the introduction into the polymerization of impurities. Such impurities include fluoride ions as well as other materials, some of which cannot be identified because of their low concentrations, but that nevertheless affect polymer quality, for example molecular weight, or color.

Various methods for recovery and/or purification of surfactant are known. U.S. Pat. No. 5,990,330 discloses precipitation of perfluoroalkanecarboxylic acid with concentrated alkaline scrubbing solution. This requires strong caustic and the recovered fluorinated carboxylic acid needs further purification before it is suitable for reuse. U.S. Pat. Nos. 3,882,153 and 4,282,162 disclose adsorption on ion-exchange resin and subsequent desorption. Such treatment uses volumes of solutions both in operation and in regeneration of the ion-exchange resin. Methods of purification of fluorinated carboxylic acid include esterification of the surfactant, which sometimes requires preliminary acidification, distillation of the ester, and then conversion to the ammonium salt (U.S. Pat. No. 5,442,097). U.S. Pat. No. 4,609,497 discloses extraction of fluorinated carboxylic acid with chlorocarbon solvent, adsorption on alumina of the fluorinated carboxylic acid from the chlorocarbon solution, separation of alumina from the chlorocarbon solution, and desorption of the fluorinated carboxylic acid from alumina with ammonium hydroxide. These are multistep processes involving organics (alcohols in esterification, chlorocarbons in extraction).

Improved methods of fluorinated carboxylic acid recovery are needed that with a minimum of steps and reagents make the fluorinated carboxylic acid suitable for reuse.

SUMMARY OF THE INVENTION

This invention provides a process for the recovery and recycle of fluorinated carboxylic acid contained in the exhaust gas produced from the drying of fluoropolymer polymerized in aqueous media containing fluorinated carboxylic acid. The process includes:

a) scrubbing the exhaust gas to produce a scrubber solution containing fluorinated carboxylic acid, b) concentrating the scrubber solution to produce a concentrated scrubber solution, c) contacting the concentrated scrubber solution with alumina to produce a recovered fluorinated carboxylic acid solution, and d) directly reusing the recovered fluorinated carboxylic acid solution in a fluoropolymerization in aqueous media.

DETAILED DESCRIPTION

It has been discovered that fluorinated carboxylic acid in the solution from fluoropolymer dryer scrubbers can be concentrated to standard levels, the concentrated scrubber solution contacted with alumina, recovered therefrom by separation, and the recovered fluorinated carboxylic acid solution directly reused in the fluoropolymerization in aqueous media with no deleterious effect on the behavior of the polymerization or on the quality of the polymer produced. By "directly" is meant that the recovered fluorinated carboxylic acid solution is used in polymerization without further purification or treatment except for such incidental steps such as adjustment of concentration or pH, heating or cooling as called for by the polymerization recipe, or combination with other ingredients as might be required by the polymerization recipe. "Directly" has no implications as to the interval in time between the treatment of concentrated scrubber solution according to this invention, and the use of the recovered fluorinated carboxylic acid solution in polymerization.

Fluoropolymers are defined herein as polymers produced in polymerization in which at least some of the constituent monomers are fluoromonomers. Fluoropolymers are further defined as containing at least about 10% fluorine by weight, preferably at least about 35% fluorine by weight. Preferred fluoromonomers are fluoroolefins. Most preferred are fluoroolefins in which at least one of the substituents on the doubly bonded carbon atoms is a fluorine atom. Aqueous polymerization is well-known in the fluoropolymer art. Examples are disclosed in U.S. Pat. Nos. 5,399,643, 4,391,940, 4,189,551, and 3,855,191. Tetrafluoroethylene (TFE) hompolymers and copolymers may be made this way. Important comonomers used with TFE are hexafluoropropylene (HFP), perfluoro(alkyl vinyl ether) (PAVE), and ethylene (E). Perfluoro(alkyl vinyl ethers) include perfluoro (propyl vinyl ether), perfluoro(ethyl vinyl ether), and perfluoro(methyl vinyl ether), as well as others in which the alkyl group is substituted with groups that can give rise to functionality, such as find use in ion-exchange polymers and as cross-linking sites in elastomers. Chlorotrifluoroethylene, trifluoroethylene, vinylidene fluoride and vinyl fluoride may also be homo- or copolymerized in aqueous media using fluorinated carboxylic acid surfactant. Typical fluoropolymers made by polymerization in aqueous media include polytetrafloroethylene (PTFE), TFE/HFP (FEP), TFE/PAVE (PFA), and E/TFE (sold by DuPont under the trademark Tefzel®).

The fluorinated carboxylic acid that is the subject of this invention is a highly fluorinated alkanecarboxylic acid or the salt thereof. By "highly fluorinated" is meant that at least about half of the substituents on the alkyl chain of the alkanecarboxylic acid are fluorine atoms. Preferably the highly fluorinated alkanecarboxylic acid is a perfluoroalkanecarboxylic acid or salt thereof, more preferably six- to twelve-carbon perfluoroalkanecarboxylic acids or salts thereof, and most preferably perfluorooctanoic acid (PFOA) or its salts, preferably the ammonium salt. PFOA in the ammonium salt form is available commercially from the 3M Company, St. Paul, Minn., USA. PFOA preparation is disclosed in U.S. Pat. No. 5,945,562. The term "fluorinated carboxylic acid" as used herein is understood to include the fluorinated carboxylic acid per se as well as the salts of the fluorinated carboxylic acid such as the ammonium salt.

The fluorinated carboxylic acid used in fluoropolymerization in aqueous media must be substantially free of impurities that can affect the polymerization or the quality of the polymer made. By "substantially free" is meant that the concentration of such impurities is sufficiently low that they do not adversely affect the polymerization or the polymer. Impurities include material that indirectly affects polymer or polymerization, such as by corrosion of the polymerization vessel so as to cause metal ion contamination of the polymerization medium or the polymer. Impurities also include material that has telegenic activity, that is that can interfere with or terminate polymer chain growth, or that has chain transfer activity. Such materials affect polymer molecular weight and molecular weight distribution, which are important properties of fluoropolymers. Impurities also include materials that affect other polymer properties, such as color. Because impurities can have deleterious effects even when present at very low levels, it is often difficult to detect their presence or determine their composition.

As stated above, a portion of the fluorinated carboxylic acid used in aqueous polymerization remains with the polymer when it is isolated from the polymerization medium. In dispersion polymerization, isolation generally involves coagulation of the dispersion, washing of the coagulated polymer, and removal of water by physical means as far as possible. The polymer is then dried by heating in a dryer or oven at temperatures from 100 to 300° C., the temperature depending upon the nature of the polymer. In the dryer, hot air or other gas passes over the polymer, removing water and other volatile materials that are present, including the fluorinated carboxylic acid, as is disclosed in U.S. Pat. No. 5,391,709. Small amounts of hydrogen fluoride and ammonia may be given off by the drying polymer. Adventitious organic material and the products to which they may be degraded during drying are also carried off in the dryer exhaust gas.

In accordance with the invention, the exhaust gas is scrubbed, preferably with demineralized water, or aqueous solution substantially free from ionic impurities, to remove the volatile materials and prevent their escape to the environment. In this way the fluorinated carboxylic acid, hydrogen fluoride, and other volatiles are captured in the scrubber solution. Scrubber solution is preferably recirculated until the fluorinated carboxylic acid concentration reaches about 500 to about 5000 parts per million by weight (ppm), more preferably about 1000 to about 4000 ppm, and most preferably about 2000 to about 3000 ppm. Foaming in the scrubber system provides a practical limit for the concentration of fluorinated carboxylic acid in the scrubber solution.

The scrubber solution is then concentrated to produce a concentrated scrubber solution. Preferably this is accomplished by passing the scrubber solution through one or more reverse-osmosis (RO) units to increase the concentration of fluorinated carboxylic acid to about 1 to about 35 wt. %, more preferably about 5 to about 30 wt. %, even more preferably about 10 to about 25 wt. %, and most preferably about 20±5 wt. %. The nature of the membrane in the RO units may require adjustment of the pH of the scrubber solution to operate efficiently. The resulting concentrated scrubber solution typically also contains several hundred ppm fluoride ion, and frequently has a color that varies from light tan to brown, indicative of other impurities, including organic impurities. The color, as measured by the APHA color test, described below, is typically from about 50 to about 300.

The fluoride ion content of the concentrated scrubber solution is generally high enough to affect the ionic strength of the polymerization medium if the solution were to be used directly. Variation in ionic strength can cause variation in the properties of the resulting dispersion and of the polymer itself, which is undesirable. Furthermore, depending upon materials of construction, fluoride ions may present corrosion problems and thereby lead to contamination of polymer. Therefore the recovered concentrated scrubber solution is contacted with alumina to reduce fluoride concentration. This may be done, for example, by passing the concentrated scrubber solution through a bed packed with alumina, the preferred method, or by slurrying the fluorinated carboxylic acid solution with alumina and then separating the solution from the alumina. This solution is referred to herein as recovered fluorinated carboxylic acid solution. The temperature of concentrated scrubber solution during the alumina treatment may be from about 5° C. to about 90° C., preferably about 10° C. to about 50° C., and more preferably about 15° C. to about 30° C. Contact time if the alumina bed method is used is somewhat dependent upon temperature but is in the range of about 5 to about 60 minutes. The concentrated scrubber solution feed to the alumina preferably has a pH of about 4 to about 7, more preferably at about 5 to about 6.

The recovered fluorinated carboxylic acid solution preferably has an APHA color below about 100, most preferably below about 50. Fluoride concentration in the recovered fluorinated carboxylic acid solution is preferably no greater than about 30 ppm, most preferably no greater than about 10 ppm. In addition, it is preferable for the recovered fluorinated carboxylic acid solution to have a pH in the range of about 4 to about 9, more preferably about 6 to about 8, so as to be is directly usable in polymerization without pH adjustment. However, with some recovery scenarios, for example, the pH may be outside this range depending upon the type of fluoropolymer from which it is recovered and the method used in coagulation of the dispersion. The pH may have been adjusted to be outside this range for RO unit efficiency. If so, where the recovered fluorinated carboxylic solution is too acidic, aqueous ammonium hydroxide is used to raise the pH to the desired range. Where the solution is too basic, aqueous sulfuric acid is used to reduce the pH to the desired range.

Commercially available forms of alumina, that is aluminum oxide, may be used. The physical size is chosen with the size of the equipment and the rates of flow in mind. Surface area is from about 100 $m^2/g$ to about 1000 $m^2/g$, preferably from about 100 $m^2/g$ to about 500 $m^2/g$.

Direct reuse of the recovered fluorinated carboxylic acid solution in a fluoropolymerization is suitably accomplished by employing known polymerization procedures in which the recovered solution is added the aqueous medium for the fluoropolymerization for all or a portion of the surfactant needed in the recipe. Depending upon the recipe, all the fluorosurfactant may be added at the start of the polymerization, or a portion may be added at the start, and the rest during polymerization.

Surprisingly, the alumina treatment is found to improve the color of the recovered fluorinated carboxylic acid solution, rendering it essentially colorless, or water-white. Even more surprising is the discovery that the recovered fluorinated carboxylic acid solution is pure enough to be used directly in fluoropolymerization in aqueous media.

EXAMPLES

Test Methods

APHA color is determined according to the description in "Standard Methods for the Examination of Water and Wastewater", published by Hach Company, (Loveland Colo. USA) using the Hach DR/2010 spectrophotometer. The test is entitled "Color, True & Apparent", and uses the platinum-cobalt method.

Fluoride ion concentration is determined using an ion-selective electrode and a Model 901 Microprocessor Ionalyzer from Orion Research, Inc. (Beverly Mass. USA).

Melt flow rates (MFR) of the fluoropolymers are determined by ASTM method D1238–52T modified as described in U.S. Pat. No. 4,380,618.

Fluoropolymer compositions are determined on 0.095–0.105 mm thick films pressed at 300° C., using Fourier transform infrared (FTIR) spectroscopy.

For hexafluoropropylene (HFP) determination, the method described in U.S. Pat. No. 4,380,618 is used. In applying this method, the absorbances of bands found at about 10.18 $\mu$m and at about 4.25 $\mu$m are used. HFP content is expressed as an HFP index (HFPI), the ratio of the 10.18 $\mu$m absorbance to the 4.25 $\mu$m absorbance. HFP content in wt % is calculated as 3.2×HFPI.

Perfluoro(ethyl vinyl ether) (PEVE) is determined from an infrared band at 9.17 $\mu$m using FTIR spectroscopy. PEVE content in wt % is calculated as 1.3×the ratio of the 9.17 $\mu$m absorbance to 4.25 $\mu$m absorbance. The absorbance at 9.17 $\mu$m is determined using a TFE/HFP dipolymer reference film to subtract a strong absorbance that overlies the 9.17 $\mu$m band. The 4.25 $\mu$m internal thickness absorbance is determined without use of reference film.

Average size of polymer particles as polymerized, i.e., raw dispersion particle size (RDPS), is measured by photon correlation spectroscopy.

Polymer color is measured according to ASTM D 6290–98. The Hunter Lab Tristimulus Color System is used. "%G" is the is the "Y" value of the XYZ measurement. "YI" is the yellowness index.

Example 1

In the course of drying a fluoropolymer made by aqueous dispersion polymerization, scrubber solution is collected and concentrated to 18.9 wt % through a series of reverse osmosis units. The resulting concentrated scrubber solution contains 146 ppm fluoride ion and has a pH of 3.5. (Subsequent experience has shown that a higher pH, for example about 4.5, is preferable for best operation of some RO units.) The concentrated scrubber solution is passed through a cylindrical vessel that is packed with alumina particles (12 to 32 mesh size, i.e. about 0.7 to 1.4 mm). The alumina-packed section of the vessel is about 16 inches (41 cm) in diameter and 84 inches (2.13 m) in height. The alumina used is UOP grade A-2 (12 to 32 mesh, 300 m$^2$/g) or A-201 (12 to 32 mesh, 320 m$^2$/g), from UOP LLC, Des Plaines, Ill. USA. The concentrated scrubber solution is fed through the bed at a rate of 0.6 gpm (0.14 m$^3$/hr). The resulting recovered fluorinated carboxylic acid solution contains 4.1 ppm fluoride ion, has a pH of 8.1, and its APHA color is 56, which is about the APHA color of water. This recovered fluorinated carboxylic acid solution is used directly as fluorosurfactant in the aqueous polymerization of TFE and HFP to make FEP. The polymerization proceeds normally and the resulting polymer meets product specifications.

Examples 2 to 5

Perfluorooctanoic acid (PFOA) is recovered from the drying of FEP and treated as described in Example 1, and the resulting material is identified as PFOA-1. A second sample is recovered from the drying of PTFE, treated as described in Example 1, and the resulting material is identified as PFOA-2. Table 1 summarizes their properties.

TABLE 1

| PFOA | Solids % | pH | Color Index | Fluoride (ppm) |
|---|---|---|---|---|
| PFOA-1 | 18.72 | 4.9 | 85 | 0.9 |
| PFOA-2 | 19.27 | 8.8 | 11 | 1.5 |

Polymerization according to the recipe of Example 1 of U.S. Pat. No. 5,700,889, adjusted to achieve lower melt flow rate, shorter polymerization time, and composition like that of Control C of that patent, is employed using PFOA-1, PFOA-2, and a commercial PFOA (Comm), as a control. Typical results with commercial PFOA, based on experience with the recipe, are given also. Table 2 summarizes the results of the polymerizations and Table 3, some properties of the polymers produced. Typical properties are included.

TABLE 2

| Example | PFOA | Polymerization Time (min) | RDPS (nm) | Dispersion pH | Solids % |
|---|---|---|---|---|---|
| 2 | Comm | 121 | 196 | 2.33 | 32.3 |
| 3 | 1 | 125 | 183 | 2.23 | 32.4 |
| 4 | 2 | 125 | 202 | 2.26 | 32.1 |
| 5 | Comm | 125 | 186 | 2.19 | 31.6 |
| Typical | — | 125 ± 10 | 190 ± 10 | 2.2 ± 0.3 | 32 ± 1 |

TABLE 3

| Example | PFOA | MFR | HFP (wt %) | PEVE (wt %) |
|---|---|---|---|---|
| 2 | Comm | 8.63 | 11.0 | 0.79 |
| 3 | 1 | 9.74 | 10.9 | 0.74 |
| 4 | 2 | 6.71 | 10.6 | 0.71 |
| 5 | Comm | 9.18 | 11.2 | 0.80 |
| Typical | — | 5 to 10 | 10.5 ± 1 | 0.75 ± 0.1 |

The polymerization proceeds normally with the PFOA processed according to this invention, and the resulting polymer also is standard for polymer made using this recipe.

Examples 6 to 8

Three aqueous dispersion polymerizations using PFOA recovered according to the procedure of this invention are run using a recipe like that of Examples 2 to 5 but adjusted to achieve a higher melt flow rate by increasing the initiator feed rate. The polymer produced is suitable for extrusion of wire insulation. Polymer properties are normal and match specifications for MFR and color of polymer made using commercial surfactant. Polymer properties are summarized in the Table 4.

TABLE 4

| | Example 6 | Example 7 | Example 8 |
|---|---|---|---|
| Ave. Particle Size ($\mu$m) | 198 | 189 | 191 |
| Melt Flow Rate (g/10 min) | 20.64 | 20.69 | 19.81 |
| % G (ASTM D 6290-98) | 55.4 | 55.7 | 55.1 |
| Yellowness Index (ASTM D 6290-98) | −4.80 | −5.00 | −4.70 |

What is claimed is:

1. A process for the recovery and recycle of fluorinated carboxylic acid contained in the exhaust gas produced from the drying of fluoropolymer that has been polymerized in aqueous media containing fluorinated carboxylic acid comprising:

a) scrubbing the exhaust gas to produce a scrubber solution containing fluorinated carboxylic acid, b) concentrating said scrubber solution to produce a concentrated scrubber solution, c) contacting the concentrated scrubber solution with alumina to produce a recovered fluorinated carboxylic acid solution, and d) directly reusing said recovered fluorinated carboxylic acid solution in a fluoropolymerization in aqueous dispersion.

2. The process of claim 1 wherein said fluorinated carboxylic acid is a perfluorinated carboxylic acid.

3. The process of claim 1 wherein said fluorinated carboxylic acid is perfluorooctanoic acid.

4. The process of claim 1 wherein said scrubbing produces a scrubber solution containing about 500 to about 5000 parts per million fluorinated carboxylic acid.

5. The process of claim 1 wherein said concentrating produces a concentrated scrubber solution containing about 1 to about 35% by weight fluorinated carboxylic acid.

6. The process of claim 1 wherein said recovered fluorinated carboxylic acid solution contains no more than about 30 parts per million fluoride ion.

7. The process of claim 1 wherein the recovered fluorinated carboxylic acid solution has an APHA color below about 100.

8. The process of claim 1 wherein the alumina has a surface area from about 100 $m^2$/g to about 1000 $m^2$/g.

9. The process of claim 1 wherein the recovered fluorinated carboxylic acid solution has a pH of about 4 to about 9.

* * * * *